(12) United States Patent
Garovic

(10) Patent No.: US 9,810,695 B2
(45) Date of Patent: *Nov. 7, 2017

(54) MARKERS FOR PREECLAMPSIA

(71) Applicant: Mayo Foundation for Medical Education and Research, Rochester, MN (US)

(72) Inventor: Vesna D. Garovic, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/408,084

(22) Filed: Jan. 17, 2017

(65) Prior Publication Data

US 2017/0122960 A1    May 4, 2017

Related U.S. Application Data

(63) Continuation of application No. 14/733,521, filed on Jun. 8, 2015, now Pat. No. 9,557,342, which is a continuation of application No. 14/312,980, filed on Jun. 24, 2014, now abandoned, which is a continuation of application No. 14/032,361, filed on Sep. 20, 2013, now abandoned, which is a (Continued)

(51) Int. Cl.
*G01N 33/536* (2006.01)
*G01N 33/80* (2006.01)
*G01N 33/68* (2006.01)

(52) U.S. Cl.
CPC .......... *G01N 33/689* (2013.01); *G01N 33/536* (2013.01); *G01N 33/80* (2013.01); *G01N 2800/368* (2013.01)

(58) Field of Classification Search
CPC .... G01N 33/74; G01N 33/80; G01N 33/6893; G01N 33/689; G01N 33/53; G01N 2800/368; G01N 2333/71; G01N 33/536
See application file for complete search history.

(56) References Cited

U.S. PATENT DOCUMENTS 5,811,250 A    9/1998  Solum et al.
6,969,591 B2   11/2005 Hara
(Continued)

FOREIGN PATENT DOCUMENTS

WO   WO2010065968   6/2010
WO   WO2011143499   11/2011
WO   WO2013181612   12/2013

OTHER PUBLICATIONS

Garovic et al. Urinary Podocyte Excretion as a Marker of Preeclampsia. America Journal of Obstetrics and Gynecology: p. 320.e1-320.e7 (Apr. 2007).*

(Continued)

*Primary Examiner* — Gail R Gabel
(74) *Attorney, Agent, or Firm* — Fish & Richardson

(57) ABSTRACT

This document provides methods and materials related to determining whether or not a pregnant mammal (e.g., a pregnant human) has preeclampsia. For example, methods and materials related to the use of urinary podocytes to determine whether or not a pregnant human has preeclampsia are provided.

5 Claims, 5 Drawing Sheets

Related U.S. Application Data continuation of application No. 12/274,117, filed on Nov. 19, 2008, now abandoned, which is a continuation-in-part of application No. 12/137,350, filed on Jun. 11, 2008, now abandoned.

(60) Provisional application No. 60/943,242, filed on Jun. 11, 2007.

(56) References Cited

U.S. PATENT DOCUMENTS

| | | | |
|---|---|---|---|
| 7,435,419 | B2 | 10/2008 | Karumanchi et al. |
| 7,455,985 | B2 | 11/2008 | Stuart et al. |
| 7,713,705 | B2 | 5/2010 | Buechler et al. |
| 9,557,342 | B2 * | 1/2017 | Garovic ............... G01N 33/74 |
| 2003/0198959 | A1 | 10/2003 | Kurnit |
| 2004/0058395 | A1 * | 3/2004 | Hara ............... G01N 33/6893 435/7.1 |
| 2006/0008804 | A1 | 1/2006 | Chibout et al. |
| 2006/0104902 | A1 | 5/2006 | Powis et al. |
| 2007/0178605 | A1 | 8/2007 | Mor et al. |
| 2008/0112960 | A1 | 5/2008 | Dorai |
| 2008/0255181 | A1 | 10/2008 | Oh et al. |
| 2008/0318836 | A1 | 12/2008 | Woolfson et al. |
| 2009/0068683 | A1 | 3/2009 | Garovic |
| 2009/0104649 | A1 | 4/2009 | Garovic |
| 2010/0158977 | A1 | 6/2010 | Zhang et al. |
| 2012/0164667 | A1 | 6/2012 | Hara et al. |
| 2013/0034861 | A1 | 2/2013 | Garovic |
| 2013/0296397 | A1 | 11/2013 | Garovic |
| 2014/0030743 | A1 | 1/2014 | Garovic |
| 2014/0051185 | A1 | 2/2014 | Garovic |
| 2014/0302538 | A1 | 10/2014 | Garovic |
| 2014/0322721 | A1 | 10/2014 | Garovic |
| 2015/0168418 | A1 | 6/2015 | Garovic |
| 2016/0060333 | A1 | 3/2016 | Garovic |
| 2017/0003299 | A1 | 1/2017 | Garovic |

OTHER PUBLICATIONS

Rosenthal et al. Podocytouria is a sensitive and specific marker for Presclampsia. Am. J. Obstet. Gynecol. 195 (6, Suppl. 1): S36, Abstract 81 (Dec. 2006).*

Karumanchi et al. Preeclampsia and the kidney: footprints in the urine. American Journal of Obstetrics & Gynecology 2 (13): 287-288 (Apr. 2007).*

Garovic et al. Glomerular expression of nephrin and synaptopodin, but not podocin, is decreased in kidney sections from women with preeclampsia. Nephrol. Dial. Transplant. 22: 1136 (Jan. 2007).*

Szeto et al. (Clin. Chim. Acta 361: 182, 2005) Nakamura et al. (Nephrol. Dial. Transplant. 15: 1379, 2000).*

Nakamura et al. (Nephrol. Dial. Transplant. 15: 1379, 2000).*

Nakamura et al. (Am. J. Med. Sci. 320: 112, 2000).*

Vogelmann et al. (Am. J. Physiol. Renal Physiol. 285: F40, 2003).*

Achenbach et al., "Parietal epithelia cells in the urine as a marker of disease activity in glomerular diseases," *Nephrol Dial Transplant.*, 23(10):3138-3145, Epub May 5, 2008.

Ahmed et al., Colocalisation of vascular endothelial growth factor and its Flt-1 receptor in human placenta, *Growth Factors*, 12(3):235-243, 1995.

Anonymous, "Report of the National High Blood Pressure Education Program Working Group on High Blood Pressure in Pregnancy," *Am. J. Obstet. Gynecol.*, 2000, 183(suppl):S1-S22.

Baelde et al., "Podocyte specific mRNA levels measured in urine of patients with preeclampsia are increased compared to healthy pregnant controls," *J Am Soc Nephrol.*, 21: 52A., Abstract F-FC225, 2010.

Barnidge et al., "Absolute quantification of the model biomarker prostate-specific antigen in serum by LC-Ms/MS using protein cleavage and isotope dilution mass spectrometry," *J Proteome Res.*, 3:644-652, May-Jun. 2004.

Barr et al., "Isotope dilution—mass spectrometric quantification of specific proteins: model application with apolipoprotein A-I," *Clin Chem.*, 42:1676-1682, Oct. 1996.

Bondar et al., "LC-MS/MS quantification of Zn-alpha2 glycoprotein: a potential serum biomarker for prostate cancer," *Clin Chem.*, 53: 673-678, Apr. 2007.

Boseman et al., "Microparticles Expressing Vascular Endothelial Growth Factor Receptor-1 (VEGR-1) Are Increased in Preeclampsia," *J. Am. Soc. Nephrol.*, 19, Abstract SA-PO2469 (2008).

Boute et al., "NPHS2, encoding the glomerular protein podocin, is mutated in autosomal recessive steroid-resistant nephrotic syndrome," *Nat Genet.*, 24(4): 349-354, Apr. 2000.

Camici, "Urinary biomarkers of podocyte injury," *Biomark Med.*, 2(6):613-616, Dec. 2008.

Camici, "Urinary detection of podocyte injury," *Biomed Pharmacother.*, 61(5):245-249, Epub May 8, 2007.

Chaiworapongsa et al., "Evidence supporting a role for blockade of the vascular endothelial growth factor system in the pathophysiology of preeclampsia," *Am J Obstet Gynecol.*, 190(6):1541-1547, Jun. 2004.

Charnock-Jones et al., "Vascular endothelial growth factor receptor localization and activation in human trophoblast and choriocarcinoma cells," *Biol Reprod.*, 51(3):524-530, Sep. 1994.

Collino et al. "Preeclamptic sera induce nephrin shedding from podocytes through endothelin-1 release by endothelial glomerular cells," *Am J Physiol Renal Physiol.*, 294(5):F1185-F1194, Epub Feb. 20, 2008.

DeLong et al., "Comparing the areas under two or more correlated receiver operating characteristic curves: a nonparametric approach," *Biometrics*, 44:837-845, Sep. 1988.

Dijkman et al., "The parietal epithelial cell is crucially involved in human idiopathic focal segmental glomerulosclerosis," *Kidney Int.*, 68(4):1562-1572, Oct. 2005.

Donoviel et al., "Proteinuria and perinatal lethality in mice lacking NEPH1, a novel protein with homology to NEPHRIN," *Mol Cell Biol.*, 21(14): 4829-4836, Jul. 2001.

Garovic et al., "Flow cytometry as a novel method for detection of podocyturia in preeclampsia," *Am J Obstet Gynecol.*, 206(1):S349-5350, Abstract 794, Jan. 31, 2012.

Garovic et al., "Mass spectrometry as a novel method for detection of podocyturia in pre-eclampsia," *Nephrol Dial Transplant.*, 28(6):1555-1561, Epub Apr. 20, 2012.

GenBank GI No. 10441644; Accession No. AAG17141.1, dated Oct. 1, 2000, 2 pages.

GenBank GI No. 110611793; Accession No. AAH46461.2, dated Aug. 18, 2006, 2 pages.

GenBank GI No. 11321634; Accession No. NP 036252.1, dated Nov. 27, 2005, 3 pages.

GenBank GI No. 116875767; Accession No. NP 003248.3, dated Oct. 31, 2006, 7 pages.

GenBank GI No. 14572521; Accession No. AAK00529.1, dated Jun. 27, 2001, 2 pages.

GenBank GI No. 2281027; Accession No. BAA21569.1, dated Jul. 24, 1997, 1 page.

GenBank GI No. 3157976; Accession No. AAC17470.1, dated Nov. 22, 2000, 2 pages.

GenBank GI No. 33323347; Accession No. AA 007403.1, dated Sep. 29, 2003, 1 page.

GenBank GI No. 33598950; Accession No. NP 005388.2, dated May 7, 2006, 3 pages.

GenBank GI No. 340237; Accession No. AAA61283.1, dated Jan. 14, 1995, 1 page.

GenBank GI No. 4503131; Accession No. NP 001895.1, dated Jun. 4, 2006, 30 pages.

GenBank GI No. 47078292; Accession No. NP 000203.2, dated Jun. 4, 2006, 25 pages.

GenBank GI No. 66277202; Accession No. NP 001018121.1, dated May 7, 2006, 3 pages.

GenBank GI No. 6682361; Accession No. AA.F23322.1, dated Jan. 8, 2000, 2 pages.

GenBank GI No. 704348; Accession No. AAC50104.1, dated Mar. 10, 1995, 2 pages.

(56) References Cited

OTHER PUBLICATIONS

GenBank GI No. 7657465; Accession No. NP 056535.1, dated Mar. 2, 2006, 2 pages.
GenBank GI No. 7657615; Accession No. NP 055440.1, dated Dec. 18, 2005, 5 pages.
GenBank GI No. 885926; Accession No. AAA82892.1, dated Dec. 4, 1995, 2 pages.
GenBank GI No. 4501881; Accession No. NP 001091.1, dated May 21, 2006, 5 pages.
GenBank GI No. 7271815; Accession No. AAF44629.1, dated Mar. 21, 2000, 1 page.
George et al., "Nephrotic syndrome after bevacizumab: Case report and literature review," *Am J Kidney Dis.*, 49(2):e23-e29, Feb. 2007.
Gonzalez-Quintero et al., "Elevated plasma endothelial microparticles in preeclampsia," *Am. J. Obstet. Gynecol.*, 189:589-593, Aug. 2003.
Gonzalez-Quintero et al., "Elevated plasma endothelial microparticles: preeclampsia versus gestational hypertension," *Am. J. Obstet. Gynecol.*, 191(4):1418-1424, Oct. 2004.
Goswami et al., "Excess syncytiotrophoblast microparticle shedding is a feature of early-onset pre-eclampsia, but not normotensive intrauterine growth restriction," *Placenta*, 27(1):56-61. Epub Jan. 25, 2005.
Habara et al., "A novel method for the estimation of podocyte injury: podocalyxin-positive elements in urine," *Folia Biol (Praha).*, 54(5):162-167, 2008.
Hara et al., "Immunohistochemical and urinary markers of podocyte injury," *Pediatr Nephrol.*, 12: 43-48, 1998.
Hirayama et al., "Podocyte Membrane Vesicles in Urine Originate from glomerular Podocyte Microvilli In Situ," *J. Am. Soc. Nephrol.*, 19, Abstract SA-PO2468, 2008.
Izzedine et al., "VEGF signalling inhibition-induced proteinuria: Mechanisms, significance and management" *Eur J Cancer.*, 46(2):439-448, Epub Dec. 16, 2009.
Jayachandran et al., "Methodology for isolation, identification and characterization of microvesicles in peripheral blood," J Immunol Methods., 375(1-2):207-214, Epub Oct. 29, 2011, print Jan. 31, 2012.
Jones, "HELLP! A Cry for Laboratory Assistance: A Comprehensive Review of the HELLP Syndrome Highlighting the Role of the Laboratory," *Hematopathol Mol Hematol.*, 11(3-4):147-171, 1998.
Kanjanabuch et al., "Urine Podocyte Predicts Steroid Responsiveness in Naive Nephrotic Syndrome," *J. Am. Soc. Nephrol.*, 19, Abstract SA-PO2467, 2008.
Kerjaschki et al., "Identification and characterization of podocalyxin—the major sialoprotein of the renal glomerular epithelial cell," *J Cell Biol.*, 98(4):1591-1596, Apr. 1984.
Kershaw et al., "Molecular cloning and characterization of human podocalyxin-like protein. Orthologous relationship to rabbit PCLP1 and rat podocalyxin," *J Biol Chem.*, 272(25):15708-15714, Jun. 20, 1997.
Kihara et al., "Podocyte detachment and epithelial cell reaction in focal segmental glomerulosclerosis with cellular variants," *Kidney Int.*, 63(52):S171-S176, Dec. 1997.
Kikuno et al., "Prediction of the Coding Sequences of Unidentified Human Genes. XIV. The Complete Sequences of 100 New cDNA Clones from Brain Which Code for Large Proteins in vitro," *DNA Res.*, 6(3):197-205, 1999.
Kiuchi-Saishin et al., "Differential expression patterns of claudins, tight junction membrane proteins, in mouse nephron segments," *J Am Soc Nephrol.*, 13(4):875-886, Apr. 2002.
Knight et al., "Shedding of syncytiotrophoblast microvilli into the maternal circulation in pre-eclamptic pregnancies," *Br J Obstet Gynaecol.*, 105(6):632-640, Jun. 1998.
Konijnenberg et al., "Extensive platelet activation in preeclampsia compared with normal pregnancy: enhanced expression of cell adhesion molecules," *Am. J. Obstetrics & Gynecology*, 176(2):461-469, Feb. 1997.

Koopman et al., "Annexin V for flow cytometric detection of phosphatidylserine expression on B cells undergoing apoptosis," *Blood*, 84(5):1415-1420, Sep. 1, 1994.
Kuzyk et al., "Multiple reaction monitoring-based, multiplexed, absolute quantitation of 45 proteins in human plasma," *Mol Cell Proteomics.*, 8(8):1860-1877, Epub May 1, 2009.
Launay-Vacher and Deray, "Hypertension and proteinuria: a class-effect of antiangiongenic therapies," *Anticancer Drugs*, 20(1):81-82, Jan. 2009.
Levine et al., "Circulating angiogenic factors and the risk of preeclampsia," *N Engl J Med.*, 350(7):672-683, Epub Feb. 5, 2004.
Levine et al., "Soluble endoglin and other circulating antiangiogenic factors in preeclampsia," *N Engl J Med.*, 355(10):992-1005, Sep. 7, 2006.
Levine et al., "Urinary placental growth factor and risk of preeclampsia," *JAMA*, 293(1):77-85, Jan. 5, 2005.
Lok et al., "Microparticle-associated P-selectin reflects platelet activation in preeclampsia," *Platelets*, 18(1):68-72, Feb. 2007.
Lok et al., "Circulating platelet-derived and placenta-derived microparticles expose Flt-1 in preeclampsia," *Reprod Sci.*, 15(10):1002-1010, Epub Oct. 20, 2008.
Martel et al., "Bevacizumab-related toxicities: association of hypertension and proteinuria," *Comm. Oncol.*, 3:90-93, Feb. 2006.
Maynard et al., "Excess placental soluble fms-like tyrosine kinase 1 (sFlt1) may contribute to endothelial dysfunction, hypertension, and proteinuria in preeclampsia," *J Clin Invest.*, 111(5):649-658, Mar. 2003.
Mundel and Shankland, "Podocyte biology and response to injury," *J Am Soc Nephrol.*, 13(12):3005-3015, Dec. 1, 2002.
Mundel et al., "Rearrangements of the cytoskeleton and cell contacts induce process formation during differentiation of conditionally immortalized mouse podocyte cell lines," *Exp Cell Res.*, 236(1): 248-258, Oct. 1997.
Mundel et al., "Synaptopodin: an actin-associated protein in telencephalic dendrites and renal podocytes," *J Cell Biol.*, 139(1): 193-204, Oct. 6, 1997.
Najafian et al., "Podocyte Detachment (PCD) Does Not Precede Idiopathic Focal Segmental Glomerulosclerosis in Children," *J. Am. Soc. Nephrol.*, 19, Abstract SA-PO2466, 2008.
Neufeld et al., "Vascular endothelial growth factor (VEGF) and its receptors," *FASEB J.*, 13(1):9-22, Jan. 1999.
Nomura et al., "Platelet-derived microparticles may influence the development of atherosclerosis in diabetes mellitus," *Atherosclerosis.*, 116(2):235-240, Aug. 1995.
Ohse et al., "Establishment of conditionally immortalized mouse glomerular parietal epithelial cells in culture," *J Am Soc Nephrol.*, 19(10):1879-1890, Epub Jul. 2, 2008.
Park et al., "An elevated maternal plasma, but not amniotic fluid, soluble fms-like tyrosine kinase-1 (sFlt-1) at the time of mid-trimester genetic amniocentesis is a risk factor for preeclampsia," *Am J Obstet Gynecol.*, 193(3 Pt 2):984-989, Sep. 2005.
Petermann et al., "Podocytes that detach in experimental membranous nephropathy are viable," *Kidney Int.*, 64:1222-1231, Oct. 2003.
Ramsuran et al., "The Role of Podocytes in the early detection of pre-eclampsia," *Cardiovascular Health.*, 2(1):43-47, Sep. 28, 2011.
Saleem et al., "A conditionally immortalized human podocyte cell line demonstrating nephrin and podocin expression," *J Am Soc Nephrol.*, 13(3):630-638, Mar. 2002.
Sarrab et al., "Establishment of conditionally immortalized human glomerular mesangial cells in culture, with unique migratory properties," *Am J Physiol Renal Physiol.*, 301(5):F1131-F1138, Epub Jun. 8, 2011.
Schiffer et al., "Apoptosis in podocytes induced by TGF-beta and Smad7," *J Clin Invest.*, 108(6):807-816, Sep. 2001.
Seegmiller et al., "Quantification of urinary albumin by using protein cleavage and LC-MS/MS," *Clin Chem.*, 55(6):1100-1107, Epub Mar. 26, 2009.
Selheim et al., "Identification of functional VEGF receptors on human platelets," *FEBS Lett.*, 512(1-3):107-110, Feb. 13, 2002.
Simon et al., "Receptors of vascular endothelial growth factor/vascular permeability factor (VEGF/VPF) in fetal and adult human

(56) References Cited

OTHER PUBLICATIONS kidney: localization and [125I]VEGF binding sites," *J Am Soc Nephrol.*, 9(6):1032-1044, Jun. 1998.

Skoberne et al., "Glomerular epithelial cells in the urine: what has to be done to make them worthwhile?" *Am J Physiol Renal Physiol.*, 296(2):F230-F241, Epub Oct 8, 2008.

Stokes et al., "Glomerular disease related to anti-VEGF therapy," *Kidney International.*, 74:1487-1491, 2008.

Sugimoto, "Neutralization of circulating vascular endothelial growth factor (VEGF) by Anti-VEGF antibodies and soluble VEGF receiptor 1 (sFit-1) induces proteinuria," *J Biol Chem.*, 278(15):12605-12608, Epub Jan. 21, 2003.

Takano et al., "Development of glomerular endothelial cells, podocytes and mesangial cells in the human fetus and infant," *Tohoku J Exp Med.*, 212(1):81-90, May 2007.

VanWijk et al., "Microparticle subpopulations are increased in preeclampsia: Possible involvement in vascular dysfunction?" *Am. J. Obsetet. Gynecol.*, 187: 450-456, Aug. 2002.

Villmow et al., "Markers of platelet activation and platelet-leukocyte interaction in patients with myeloproliferative syndromes," *Thromb Res.*, 108(2-3):139-145, Nov. 1, 2002.

Wang et al., "Increased urinary excretion of nephrin, podocalyxin, and βig-h3 in women with preeclampsia," *Am J Physiol Renal Physiol.*, 302(9):F1084-F1089, Epub Feb. 1, 2012.

Yu et al., "Urinary podocyte loss is a more specific marker of ongoing glomerular damage than proteinuria," *J Am Soc Nephrol.*, 16(6):1733-1741, Epub Apr. 13, 2005.

Zand et al., "Urinary Microvesicles Detect Podocyte Injury in Diabetic Nephropathy," American Society of Nephrology Kidney Week 2013, Atlanta, GA, Nov. 5-10, 2013, JASN Abstract Supplement, J Am Soc Nephrol., 24: 188A, TH-PO378, 2013.

Zand et al., "Urinary Microvesicles Differentiate Patients with Diabetic Nephropathy from Those with Active Glomerulonephritis," American Society of Nephrology Kidney Week 2013, Atlanta, GA, Nov. 5-10, 2013, JASN Abstract Supplement, *J Am Soc Nephrol.*, 24: 805A, SA-PO774, 2013.

Zhao et al., "Altered nephrin and podoplanin distribution is associated with disturbed polarity protein PARD-3 and PARD-6 expressions in podocytes from preeclampsia," *Reprod Sci.*, 18(8):772-780, Epub Mar. 21, 2011.

Zhu et al., "Risks of proteinuria and hypertension with bevacizumab, an antibody against vascular endothelial growth factor: systematic review and meta-analysis," *Am J Kidney Dis.*, 49(2):186-193, Feb. 2007.

Zwaal et al., "Pathophysiologic implications of membrane phospholipid asymmetry in blood cells," *Blood*, 89(4):1121-1132, Feb. 15, 1997.

European Communication Pursuant to Article 94(3) EPC in Application No. 13796896.2 dated Nov. 28, 2016, 4 pages.

European Office Action in Application No. 10842718.8 dated Jul. 12, 2013, 5 pages.

European Search Report for App. No. 13796896.2, dated Dec. 21, 2015, 6 pages.

European Search Report in Application No. 10842718.8 dated Jun. 19, 2013, 2 pages.

International Preliminary Report on Patentability for PCT/US2013/043727, dated Dec. 11, 2014, 5 pages.

International Preliminary Report on Patentability for PCT/US2014/064007, dated Jun. 9, 2016, 8 pages.

International Preliminary Report on Patentability in PCT/US2009/064934, dated Jun. 3, 2011, 5 pages.

International Preliminary Report on Patentability in PCT/US2010/061543, dated Jun. 26, 2012, 5 pages.

International Search Report and Written Opinion for PCT/US2014/064007, dated Jan. 21, 2015, 14 pages.

International Search Report and Written Opinion in PCT/US2009/064934 dated Jul. 9, 2010, 5 pages.

International Search Report and Written Opinion in PCT/US2010/061543, dated Sep. 29, 2011, 8 pages.

International Search Report and Written Opinion in PCT/US2013/043727, dated Oct. 18, 2013, 6 pages.

Office Action in Australian Application No. 2010339723, dated Oct. 26, 2013, 3 pages.

Office Action in Canadian Application No. 2,785,273, dated Jan. 24, 2017, 5 pages.

Office Action in Japanese App. No. 2012-546149, dated Jul. 23, 2014, 4 pages.

Office Action in U.S. Appl. No. 12/137,350, dated Mar. 11, 2013, 8 pages.

Office Action in U.S. Appl. No. 12/137,350, dated May 27, 2011, 8 pages.

Office Action in U.S. Appl. No. 12/137,350, dated Jun. 23, 2010, 8 pages.

Office Action in U.S. Appl. No. 12/137,350, dated Aug. 17, 2012, 7 pages.

Office Action in U.S. Appl. No. 12/137,350, dated Nov. 24, 2010, 9 pages.

Office Action in U.S. Appl. No. 12/137,350, dated Nov. 25, 2011, 8 pages.

Office Action in U.S. Appl. No. 12/274,117, dated Mar. 22, 2013, 11 pages.

Office Action in U.S. Appl. No. 12/274,117, dated Jun. 23, 2010, 11 pages.

Office Action in U.S. Appl. No. 12/274,117, dated Jun. 27, 2011, 13 pages.

Office Action in U.S. Appl. No. 12/274,117, dated Nov. 26, 2010, 11 pages.

Office Action in U.S. Appl. No. 12/274,117, dated Dec. 21, 2011, 8 pages.

Office Action in U.S. Appl. No. 14/019,895, dated Dec. 6, 2013, 13 pages.

Office Action in U.S. Appl. No. 14/032,361, dated Dec. 24, 2013, 23 pages.

Office action in U.S. Appl. No. 14/404,413, dated Sep. 2, 2016, 33 pages.

\* cited by examiner

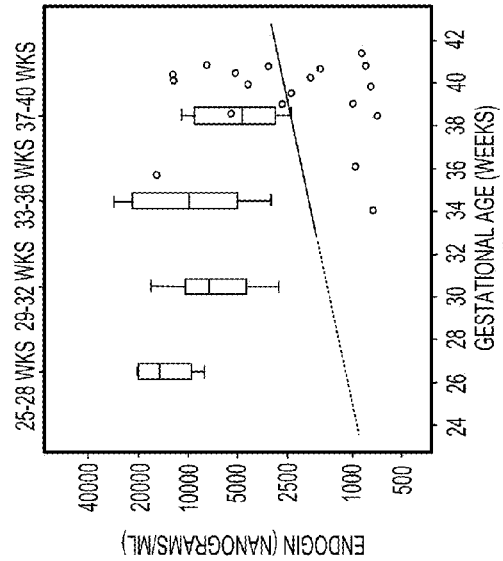
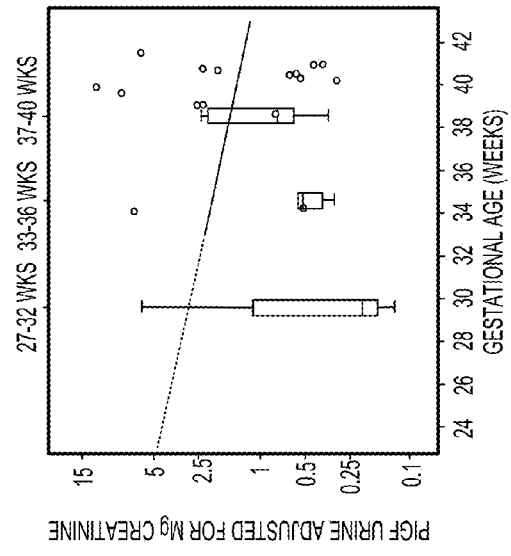
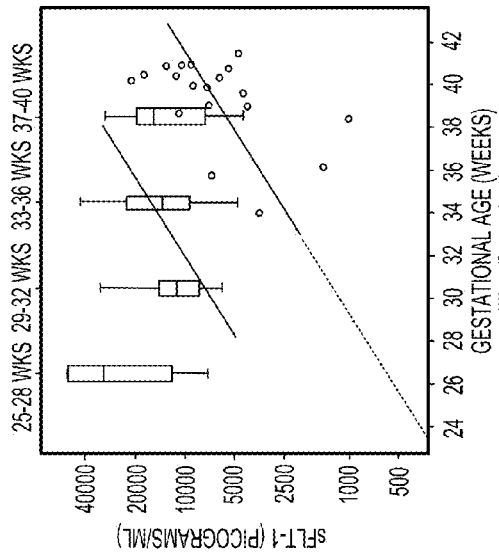
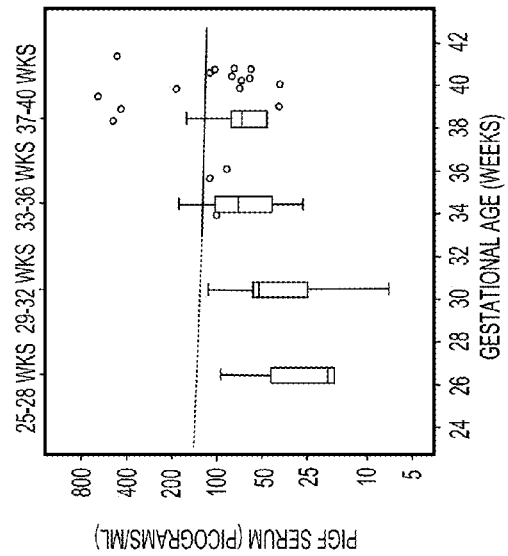
FIG. 3A
FIG. 3B
FIG. 3C
FIG. 3D

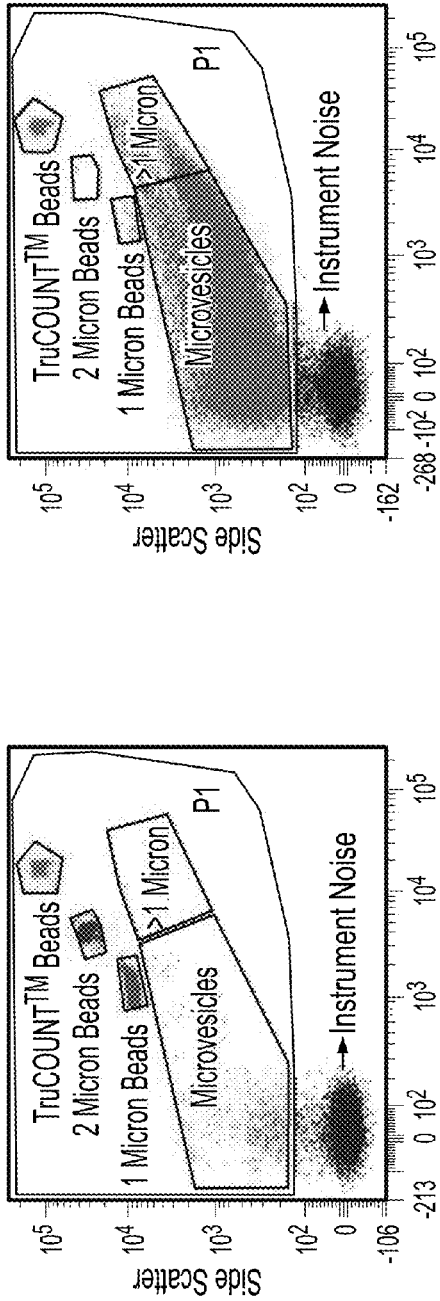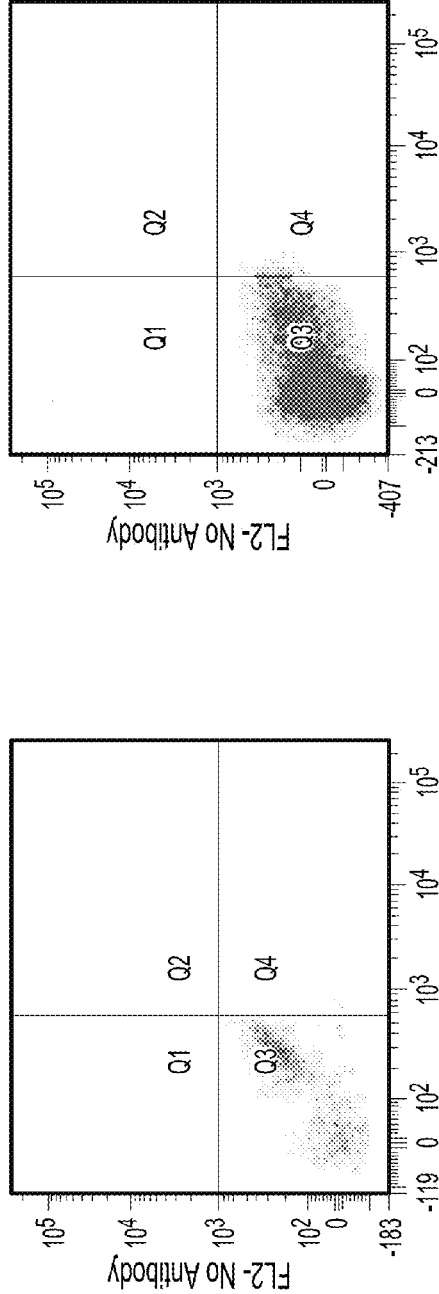

MARKERS FOR PREECLAMPSIA

CROSS-REFERENCE TO RELATED APPLICATIONS

This application is a continuation of U.S. application Ser. No. 14/733,521, filed Jun. 8, 2015 know U.S. Pat. No. 9,557,342), which is a continuation of U.S. application Ser. No. 14/312,980 (Abandoned), filed Jun. 24, 2014, which is a continuation of U.S. application Ser. No. 14/032,361 (Abandoned), filed Sep. 20, 2013, which is a continuation of U.S. application Ser. No. 12/274,117 (Abandoned), filed Nov. 19, 2008, which is a continuation-in-part of U.S. application Ser. No. 12/137,350 (Abandoned), filed Jun. 11, 2008, which claims the benefit of U.S. Provisional Application Ser. No. 60/943,242, filed Jun. 11, 2007. The disclosures of the prior applications are incorporated by reference in entirety.

STATEMENT AS TO FEDERALLY SPONSORED RESEARCH

This invention was made with government support under grant HD051714 awarded by the National Institutes of Health. The government has certain rights in the invention.

BACKGROUND

1. Technical Field

This document relates to methods and materials involved in determining whether or not a pregnant mammal has preeclampsia. For example, this document provides methods and materials related to the use of urinary podocytes and/or plasma microvesicles to determine whether or not a pregnant mammal (e.g., a pregnant human) has preeclampsia.

2. Background Information

Preeclampsia is a pregnancy-specific disease that affects about 5 percent of all pregnancies and remains a leading cause of both maternal and fetal morbidity and death worldwide. It is characterized by hypertension (blood pressure, ≥140/90 mm Hg) and proteinuria (≥300 mg in a 24-hour urine sample) that occur after 20 weeks of gestation. Proteinuria in preeclampsia is associated with characteristic renal pathologic changes of glomerular endotheliosis, which is considered to be a hallmark of preeclampsia in humans.

SUMMARY

This document relates to methods and materials involved in determining whether or not a pregnant mammal has preeclampsia. For example, this document provides methods and materials related to the use of urinary podocytes and/or plasma microvesicles to determine whether or not a pregnant mammal (e.g., a pregnant human) has preeclampsia. Identifying patients who have preeclampsia can allow such patients, who are at risk for both maternal and fetal morbidity and death, to be treated effectively. In addition, identifying patients who do not have preeclampsia can avoid unnecessary treatment and patient suffering. As described herein, the presence of urinary podocytes and/or plasma microvesicles can be used to identify pregnant humans as having preeclampsia.

In general, one aspect of this document features a method for assessing a pregnant mammal for preeclampsia. The method comprises, or consists essentially of, determining whether or not a urine sample from the mammal contains an elevated level of urinary podocytes, wherein the presence of the elevated level indicates that the mammal has preeclampsia. The mammal can be a human. The determining step can comprise using an antibody to detect podocytes. The antibody can be an anti-podocin antibody. The antibody can be an anti-podocalyxin antibody. The antibody can be an anti-nephrin antibody. The antibody can be an anti-synaptopodin antibody. The method can comprise classifying the mammal as having preeclampsia if the elevated level is present, and classifying the mammal as not having preeclampsia if the elevated level is not present. In general, one aspect of this document features a method for assessing a pregnant mammal for preeclampsia. The method comprises, or consists essentially of, determining whether or not a plasma sample from the mammal contains an elevated level of microvesicles expressing a VEGFR-1 polypeptide, and classifying the mammal as having preeclampsia if the plasma contains the elevated level. The mammal can be a human. The determining step can comprise using flow cytometry. The determining step can comprise using an antibody to detect the microvesicles. The antibody can be an anti-VEGFR-1 antibody. The method can comprise classifying the mammal as having preeclampsia if the elevated level is present, and can comprise classifying the mammal as not having preeclampsia if the elevated level is not present.

In another aspect, this document features a method for assessing a mammal for risk of developing a complication of preeclampsia. The method comprises, or consists essentially of, determining whether or not plasma from the mammal contains an elevated level of endothelium-derived microvesicles and classifying the mammal as being at risk for developing a complication of preeclampsia. The determining step can comprise using flow cytometry. The determining step can comprise using an antibody to detect the endothelium-derived microvesicles. The complication of preeclampsia can comprise HEELP syndrome. The method can comprise classifying the mammal as being at risk of developing a complication of preeclampsia if the elevated level is present, and can comprise classifying the mammal as not being at risk of developing a complication of preeclampsia if the elevated level is not present.

In another aspect, this document features a method for assessing a pregnant mammal for preeclampsia. The method comprises, or consists essentially of, determining whether or not a urine sample from the mammal contains an elevated level of urinary podocytes, wherein the presence of the elevated level indicates that the mammal has preeclampsia. The mammal can be a human. The determining step can comprise using an antibody to detect podocytes. The antibody can be an anti-podocin antibody. The antibody can be an anti-podocalyxin antibody. The antibody can be an anti-nephrin antibody. The antibody can be an anti-synaptopodin antibody. The method can comprise classifying the mammal as having preeclampsia if the elevated level is present, and classifying the mammal as not having preeclampsia if the elevated level is not present.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 3A-3D contain graphs plotting sFlt-1 (FIG. 3A; pg/mL), soluble endoglin (FIG. 3B; ng/mL), serum PIGF (FIG. 3C; pg/mL), and urine PIGF (FIG. 3D; adjusted for Mg creatinine) for normotensive and preeclamptic pregnancies as a function of age. For normotensive pregnancies, open circles indicate individual values with a trend regression line. The dashed portion represents extrapolation. For preeclamptic pregnancies, values are stratified by intervals of gestational age in which data distributions are summarized with box plots indicating median values and interquartile ranges.

FIGS. 5A-5D contain representative scatter plots obtained by FACSCanto™ flow cytometry showing control gates of buffer with fluorescein-conjugated antibodies and calibration beads (size and True Count Beads™) in the absence of sample (FIG. 5A), gates derived from adding a sample containing microvesicles to the buffer with fluorescein conjugated antibodies and calibration beads (FIG. 5B), and representative quadrants derived from the microvesicle gates shown in FIGS. 5A and 5B, respectively, with counts separated by antibody binding, and quadrant 3 representing microvesicles (FIGS. 5C and 5D).

DETAILED DESCRIPTION

Figure 1A:
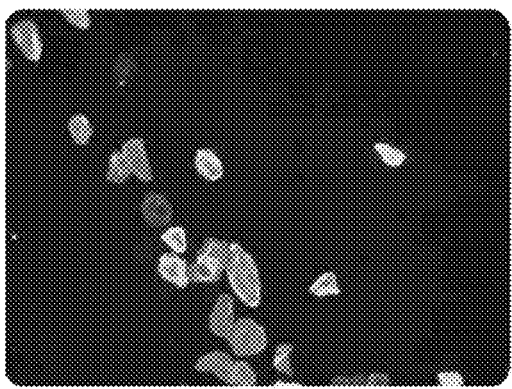
FIGS. 1A-1D contain photographs of urinary cells plated on collagen-coated slides, cultured for 24 hours, and stained for podocin (FIG. 1A), podocalyxin (FIG. 1B), nephrin (FIG. 1C), and synaptopodin (FIG. 1D) immunoreactivity.

This document provides methods and materials related to determining whether or not a pregnant mammal (e.g., a pregnant human) has preeclampsia. For example, this document provides methods and materials related to the use of urinary podocytes and/or plasma microvesicles to determine whether or not a pregnant human has preeclampsia. As described herein, if the level of urinary podocytes is elevated in a pregnant mammal, then the mammal can be classified as having preeclampsia. If the level of urinary podocytes is not elevated in a pregnant mammal, then the mammal can be classified as not having preeclampsia.

This document also provides methods and materials for using microvesicles to determine whether or not a pregnant mammal has preeclampsia. For example, a marker for preeclampsia can be an elevated level of microvesicles positive for a vascular endothelial growth factor/vascular permeability factor receptor-1 (VEGFR-1) polypeptide in a sample taken from a pregnant mammal. As disclosed herein, if the level microvesicles expressing a VEGFR-1 polypeptide in a sample from a pregnant mammal is elevated, then the mammal can be classified as having preeclampsia. If the level microvesicles expressing a VEGFR-1 polypeptide is not elevated, then the mammal can be classified as not having preeclampsia.

Microvesicles, which circulate in the peripheral blood, are a heterogeneous population of spheres (vary in size from about 0.1 to 1.5 µm) formed from intact phospholipid rich membranes. Typically, a microvesicle contains at least half of the surface polypeptides, receptors, and lipids of their cells of origin. Microvesicles are differentiated from microparticles, the latter of which can refer to chemical particles or aggregates such as those formed from plasma lipoprotein or other chemicals. Micro-vesicles are smaller than platelets, which are typically between 2 and 2.5 µm in diameter, and are generated during cell activation and apoptosis induced by oxidative damage, inflammatory cytokines and chemokines, thrombin, bacterial lipopolysaccharide, shear stress, and hypoxia.

Any appropriate type of sample can be used to evaluate the level of microvesicles in a mammal including, without limitation, serum, blood, and plasma. In addition, any method can be used to obtain a sample. For example, a blood sample can be obtained by peripheral venipuncture. Once obtained, a sample can be manipulated prior to measuring the level of microvesicles. For example, a blood sample can be centrifuged to separate serum and plasma, and the separated serum and plasma can be liquid frozen for future analysis. Once obtained, the sample can be analyzed by flow cytometry based on size or using antibodies to determine the total number of microvesicles, the level of microvesicles of a particular cellular origin, or the level VEGFR-1 expressing microvescicles, present within a sample.

This document also provides methods and materials related to the use of microvesicles to determine whether or not a pregnant mammal is at risk for developing complications associated with preeclampsia (e.g., HEELP syndrome). As described herein, if the level of endothelium-derived microvesicles is elevated in a sample taken from a pregnant mammal, then the pregnant mammal can be classified as being at risk for developing a complication of preeclampsia. If the level of endothelium-derived microvesicles is not elevated in a sample taken from a pregnant mammal, then the pregnant mammal can be classified as not being at risk for developing a complication of preeclampsia.

The methods and materials provided herein can be used to assess any pregnant mammal for preeclampsia, or a complication of preeclampsia. For example, a human, cat, dog, or horse can be assessed for preeclampsia. In some cases, a human pregnant for 18 to 36 weeks (e.g., between 18 and 35 weeks, between 20 and 35 weeks, or between 20 and 30 weeks) can be assessed.

Any appropriate method can be used to determine the level of podocytes, or any fragment of podocytes, in a mammal's urine. For example, cell staining techniques that include using antibodies that bind to podocytes or polypeptides expressed by podocytes can be used. Examples of such antibodies include, without limitation, antibodies that have the ability to bind podocin, podocalyxin, nephrin, synaptopodin, Neph1, GLEPP1, WT1, CD2AP, actin, actinin, cadherin, catenin, integrin, vinculin, talin, paxillin, and ZO-1.

Any appropriate method can be used to determine the presence of microvesicles in a sample obtained from a pregnant mammal. In some cases, the methods and materials provided herein can be used to detect microvesicles generated in vivo from many cell types. For example, a FACSCanto™ (New fourth or fifth generation) machine with high sensitivity and six colors detectors can be used to detect microvesicles. In some cases, blood can be prepared for analysis as follows. The sample can be centrifuged (e.g., 3000 g for 15 minutes). The resulting supernatant from this spin can be removed and re-spun (e.g., using the same speed and duration). The absence of platelets from the supernatant of the second spin can be validated by Coulter counter. This platelet free plasma can be centrifuged (e.g., 20,000 g for 30 minutes), and the pellet can be washed (e.g., washed once with HEPES/Hanks buffer) and centrifuged (e.g., 20,000 g for 30 minutes) to prepare washed microvesicles. The supernatant can be discarded, and the pellet reconstituted with buffer (e.g., HEPES/Hanks buffer). These microvesicles can be stained to identify their cell of origin (all cells, not only platelets). Higher than 95% of microvesicles that circulate in the blood of healthy people can originate from platelets. Both buffers and antibodies can be filtered through 0.2 µm filters to remove contaminants before staining the isolated microvesicles. The signal to noise ratio can be high (e.g., 15-30,000 events:200-500 events). Scanning and transmission electron microscopy and Cyto viva can be used to verify the presence of microvesicles.

Any appropriate method can be used to determine the level of microvesicles, present within a sample, that express, for example, a marker such as a VEGFR-1 polypeptide. For example, standards such as those described herein (e.g., anti-VEGFR-1 antibodies) can be used to identify and quantify microvesicles expressing of a VEGFR-1 polypeptide present within a sample. In some cases, the expression of a VEGFR-1 polypeptide on particular microvesicles (e.g., platelet-derived microvesicles, procoagulant microvesicles, or endothelium-derived microvesicles) can be determined using antibodies as markers associated with particular cell types. In some cases, antibodies against the markers set forth in Table 1 can be used to identify and quantify microvesicles of a particular cell origin that express VEGFR-1 polypeptides using flow cytometry techniques. For example, anti-CD62e can be used to identify endothelium-derived microvesicles present within a sample.

Any appropriate method can be used to determine the cellular origin of microvesicles present within a sample. For example, standards such as those described herein (e.g., beads of known size or cellular membrane antibodies) can be used to identify and quantify microvesicles present within a sample. In some cases, the level of particular microvesicles (e.g., platelet-derived microvesicles, procoagulant microvesicles, or endothelium-derived microvesicles) can be determined using antibodies to detect markers associated with particular cell types. For example, antibodies against the markers set forth in Table 1 can be used to identify and quantify particular microvesicles using flow cytometry techniques. In some cases, anti-CD62e can be used to identify endothelium-derived microvesicles present within a sample.

The term "elevated level" as used herein with respect to the level of urinary podocytes is any level that is above a median urinary podocytes level in urine from a random population of pregnant mammals (e.g., a random population of 10, 20, 30, 40, 50, 100, or 500 pregnant mammals) lacking preeclampsia. In some cases, an elevated level of urinary podocytes can be a detectable level of podocin-positive cells within a urine sample. The presence or absence of such a detectable level of podocin-positive cells can be determined using an anti-podocin antibody.

The term "elevated level" as used herein with respect to the level microvesicles expressing a VEGFR-1 polypeptide is any level that is greater than a control level of microvesicles expressing a VEGFR-1 polypeptide associated with a sample of microvesicles from normal, healthy mammals lacking signs or symptoms of preeclampsia. In some cases, an elevated level of VEGFR-1 expressing microvesicles can be a detectable level. In some cases, an elevated level of VEGFR-1 expressing microvesicles can be any level that is greater than a reference level for an elevated level of VEGFR-1 expressing microvesicles. For example, a reference level of microvesicles expressing a VEGFR-1 polypeptide can be the average level of microvesicles expressing a VEGFR-1 polypeptide that is present in samples obtained from a random sampling of 50 healthy pregnant mammals matched for age. It will be appreciated that levels from comparable samples are used when determining whether or not a particular level is an elevated level.

An elevated level of VEGFR-1 expressing microvesicles can be any level provided that the level is greater than a corresponding reference level of VEGFR-1 expressing microvesicles. For example, an elevated level of VEGFR-1 expressing microvesicles can be 0.5, 1, 2, 3, 4, 5, 6, 7, 8, 9, 10, 15, 20, or more times greater than the reference level VEGFR-1 expressing microvesicles. In addition, a reference level can be any amount. For example, a reference level for VEGFR-1 expressing microvesicles can be zero. In this case, any level of microvesicles expressing a VEGFR-1 polypeptide greater than zero would be an elevated level.

The term "elevated level" as used herein with respect to the level of endothelium-derived microvesicles is any level that is greater than a control endothelium-derived microvesicle level associated with mammals lacking signs or symptoms of preeclampsia, or a complication of preeclampsia. In some cases, an elevated level of endothelium-derived microvesicles can be a detectable level. In some cases, an elevated level of endothelium-derived microvesicles can be any level that is greater than a reference level for endothelium-derived microvesicles.

The term "reference level" as used herein with respect to an endothelium-derived microvesicle level is the level of endothelium-derived microvesicles typically found in healthy mammals, for example, mammals free of signs and symptoms of preeclampsia, or complications of preeclampsia. For example, a reference level of endothelium-derived microvesicles can be the average level of endothelium-derived microvesicles that is present in samples obtained from a random sampling of 50 healthy pregnant mammals matched for age. It will be appreciated that levels from comparable samples are used when determining whether or not a particular level is an elevated level.

An elevated level of endothelium-derived microvesicles can be any level provided that the level is greater than a corresponding reference level for endothelium-derived microvesicles. For example, an elevated level of endothelium-derived microvesicles can be 0.5, 1, 2, 3, 4, 5, 6, 7, 8, 9, 10, 15, 20, or more times greater than the reference level for endothelium-derived microvesicles. In addition, a reference level can be any amount. For example, a reference level for endothelium-derived microvesicles can be zero. In this case, any level of endothelium-derived microvesicles greater than zero would be an elevated level.

TABLE 1

Markers for identifying the source of microvesicles.

| Cell-derived microvesicles | Markers |
| --- | --- |
| Procoagulant microvesicles | Annexin-V or thrombin generation assay |
| Leukocytes-derived microvesicles | CD45, CD11b |
| Granulocytes-derived microvesicles | CD33, CD15, CD11b; CD177 |
| NK cells-derived microvesicles | CD56 |

TABLE 1-continued

Markers for identifying the source of microvesicles.

| Cell-derived microvesicles | Markers |
| --- | --- |
| Monocytes-derived microvesicles | CD14 |
| T-lymphocyte-derived microvesicles | CD3 and CD134 |
| B-lymphocyte-derived microvesicles | CD19 or CD20 |
| Platelet-derived microvesicles | CD41 or CD61 or CD42a |
| Endothelium-derived microvesicles | CD62e, CD106, CD146 |
| Erythrocyte-derived microvesicles | Glycophorin A |

An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type (e.g., IgG, IgM, IgD, IgA or IgY), class (e.g., IgG1, IgG4, or IgA2), or subclass. In addition, an antibody can be from any animal including birds and mammals. For example, an antibody can be a human, rabbit, sheep, or goat antibody. An antibody can be naturally occurring, recombinant, or synthetic. Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a gene encoding the partial antibody sequence. An anti-podocin antibody can bind to podocin polypeptides at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

Once the level of urinary podocytes, endothelium-derived microvesicles, or all microvesicles expressing a VEGFR-1 polypeptide in a sample from a mammal is determined, then the level can be compared to a median level or a cutoff level and used to evaluate the mammal for preeclampsia, or risk of developing a complication of preeclampsia. A level of urinary podocytes, VEGFR-1 expressing microvesicles, or endothelium-derived microvesicles that is higher than the median level of urinary podocytes, VEGFR-1 expressing microvesicles, or endothelium-derived microvesicles in samples taken from a population of mammals of the same species having no preeclampsia (or a cutoff level) can indicate that the mammal has preeclampsia, or at risk for developing a complication of preeclampsia. A level of urinary podocytes, VEGFR-1 expressing microvesicles, or endothelium-derived microvesicles that is lower than the median level of urinary podocytes, VEGFR-1 expressing microvesicles, or endothelium-derived microvesicles in samples taken from a population of mammals of the same species having no preeclampsia (or a cutoff level) can indicate that the mammal does not have preeclampsia, or is not a risk of developing a complication of preeclampsia. A cutoff level can be set to any level provided that the values greater than that level correlate with an increased level of urinary podocytes, VEGFR-1 expressing microvesicles, or endothelium-derived microvesicles indicative of a mammal having preeclampsia. For example, a cutoff level can be equal to, or greater than 1 cell/mg creatinine.

In some cases, a pregnant mammal can be classified as having preeclampsia if it is determined that the podocyte level in a urine sample from the mammal is greater than the podocyte level in a urine sample obtained previously from that mammal. In some cases, a pregnant mammal can be classified as having preeclampsia if it is determined that the level of VEGFR-1 expressing microvesicles in a sample is greater than the level of VEGFR-1 expressing microvesicles in a sample obtained previously from that mammal. In some cases, a pregnant mammal can be classified as being at risk for developing a complication of preeclampsia if it is determined that the endothelium-derived microvesicles level in a sample from the mammal is greater than the endothelium-derived microvesicles level in a urine sample obtained previously from that mammal.

A mammal that has been or is being treated for preeclampsia can be monitored using the methods and materials provided herein. For example, the level of podocytes, VEGFR-1 expressing microvesicles, or endothelium-derived microvesicles in a sample from a mammal being treated for preeclampsia can be assessed to determine whether or not the mammal is responding to the treatment.

This document also provides methods and materials to assist medical or research professionals in determining whether or not a pregnant mammal has preeclampsia. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the level of urinary podocytes in a urine sample, the level of endothelium-derived microvesicles, or the level of VEGFR-1 expressing microvesicles, and (2) communicating information about the level to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

The invention will be further described in the following examples, which do not limit the scope of the invention described in the claims.

EXAMPLES

Example 1—Urinary Podocyte Excretion as a Marker for Preeclampsia

An approved study was conducted with the consent of all included women. A diagnosis of preeclampsia was made in the presence of (a) hypertension after 20 weeks of gestation, which was defined as a blood pressure of ≥140/90 mm Hg, (b) proteinuria, which was defined as ≥300 mg of protein in a 24-hour urine specimen, and/or 1+(30 mg/L) dipstick urinalysis in the absence of urinary tract infection and/or a predicted 24-hour urine protein of ≥300 mg on a random urine collection, and (c) resolution of hypertension and proteinuria by 12 weeks after delivery. Women with severe forms of preeclampsia such as eclampsia and HELLP (hemolysis, elevated liver enzymes, low platelets) syndrome, the diagnosis of which was confirmed on the basis of previously published criteria (Jones, *Hematopathol. Mol. Hematol.*, 11:147-71 (1998)), also were included. Healthy, normotensive pregnant women without hypertension and proteinuria served as control subjects. An additional control group consisted of women with hypertension and proteinuria.

A cross-sectional study was conducted, and blood and urine samples were collected close to and typically ≤24 hours before delivery. In total, 67 women were recruited. Preeclampsia was present in 33 of the patients, and HELLP was diagnosed in 11 patients; 23 normotensive pregnancies served as control subjects (Table 1). Blood samples were obtained in all 67 women, and urine samples for podocyturia were collected in a subset of 31 pregnant women (15 cases and 16 control subjects).

TABLE 1

Patient characteristics.

| Variable | Normal (n = 23) | Preeclampsia (n = 33) | HELLP (n = 11) | Preeclampsia + HELLP (n = 44) |
| --- | --- | --- | --- | --- |
| Maternal age (y) | 28.7 ± 5.4 | 26.2 ± 5.1 | 33.0 ± 6.0 | 27.9 ± 6.1 |
| Gestational age (wk) | 39.2 ± 2.2 | 34.3 ± 3.8* | 33.5 ± 5.6* | 34.1 ± 4.2* |
| Primiparous (%) | 47.8 | 81.8 | 9.1 | 63.6 |
| Systolic blood pressure (mm Hg) | 110.5 ± 9.5 | 159 ± 19.8* | 162.6 ± 23* | 159.9 ± 20.3* |
| Diastolic blood pressure (mm Hg) | 66.9 ± 9.8 | 97.8 ± 9.4* | 98.3 ± 10.6* | 97.9 ± 9.6* |
| Proteinuria (g/24 hr) | 247 ± 294 | 2693 ± 3164* | 4373 ± 5962* | 3113 ± 4032* |
| Platelet count | 242,000 ± 35,519 | 232,333 ± 66,787 | 100,273 ± 42,245* | 199,318 ± 84,146 |

Data are given as mean ± SD.
*P < .05, compared with normal group.

Serum Studies

Blood samples for the determination of sFlt-1, free PlGF, and soluble endoglin levels were drawn within 24 hours before delivery. Serum creatinine level, liver function tests, and platelet counts were performed according to standardized laboratory procedures. Serum levels of sFlt-1, soluble endoglin, and free PlGF were measured with Quantikine ELISA (enzyme-linked immunosorbent assay) kits (R&D Systems, Minneapolis, Minn.).

Urine Chemistry

Concurrent with serum collection, clean-catch urine specimens (50-100 mL) were obtained. Urine albumin, total protein, and creatinine concentrations were measured by standard methods on a Hitachi 911 Chemistry Analyzer (Roche Diagnostics, Indianapolis, Ind.). Urinary PlGF determinations were performed with the PlGF ELISA (enzyme linked immunosorbent assay) kit (R&D Systems).

Podocyturia

Random urine samples (25-50 mL each) were centrifuged for 8 minutes at 700 g at room temperature. The pellets were rinsed twice with human diploid fibroblast (HDF) solution. Next, the pellets were resuspended in Dulbecco's modified eagle's medium (DMEM) F-12 medium with 10% fetal bovine serum that was supplemented with antibiotics for the prevention of bacterial contamination. One-milliliter aliquots were plated in four-chamber, collagen-coated tissue culture slides, which was followed by overnight incubation at 37° C. in 5% $CO_2$. The next day, the media were removed, followed by two phosphate-buffered saline solution washes. Slides were fixed with 1 mL of ice cold methanol for 10 minutes at −20° C. Each of the four slide chambers was incubated with one of four different antibodies to podocyte proteins:podocalyxin (dilution, 1:40), podocin (dilution, 1:200), nephrin (dilution, 1:100), and synaptopodin (undiluted). After being washed with phosphate-buffered saline solution, a secondary fluorescein isothiocyanate-labeled antibody was added at a dilution of 1:40 for 30 minutes. The sediment was counterstained with Hoechst nuclear stain to facilitate differentiation of whole cells from cell fragments. Coverslips were mounted with Vectashield (Vector Labs, Burlington, Calif.), and the slides were viewed with a fluorescence microscope (Leica, Germany). Nucleated, positive-staining cells were considered to be podocytes. A renal pathologist, who was blinded to the clinical diagnosis and laboratory findings, evaluated each sample to determine the number of cells that were present and the percentage of cells that were stained for podocyte markers. Podocyturia was expressed as a ratio of the number of podocytes to the creatinine content of the respective urine sample, which was performed for each of the four podocyte markers.

Statistical Methods

Descriptive statistics are reported for quantitative traits as means and SDs or as medians and interquartile ranges and for categoric traits as percentages. The operating characteristics of podocyte and angiogenic markers of preeclampsia were assessed by consideration of the trait either as a categoric measure (i.e., absence/presence) and estimation of its sensitivity and specificity or by the consideration of it as a quantitative measure and the generation of the receiver-operating characteristic (ROC) curve. The areas under the curve were estimated with confidence intervals and contrasted among markers with a method described elsewhere (DeLong et al., *Biometrics*, 44:837-45 (1988)). All statistical tests were carried out at the two-sided 0.05 significance level.

Podocyturia

In the women with urinary measures of podocyturia (i.e., 15 cases and 16 control subjects), those women with preeclampsia or HELLP had podocin-positive cells in the urine (FIG. 1A), whereas none of the normotensive control subjects had any podocin-positive cells. Thus, the sensitivity and specificity of podocyturia, as determined by the podocin-positive cells, for the diagnosis of preeclampsia were both 100%. A positive correlation between the degree of proteinuria and podocyturia, as determined by podocin staining, was present (P=0.04).

Figure 1B:
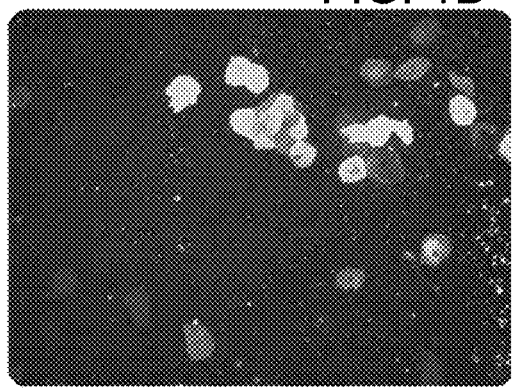
Figure 1C:
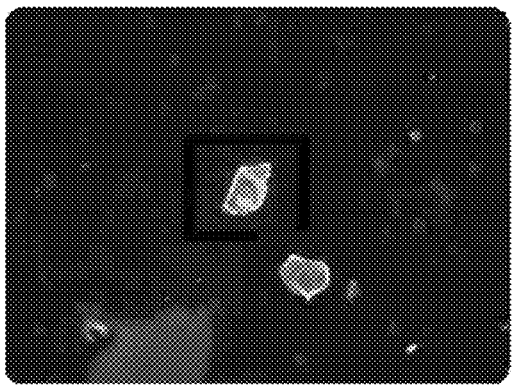
Figure 1D:
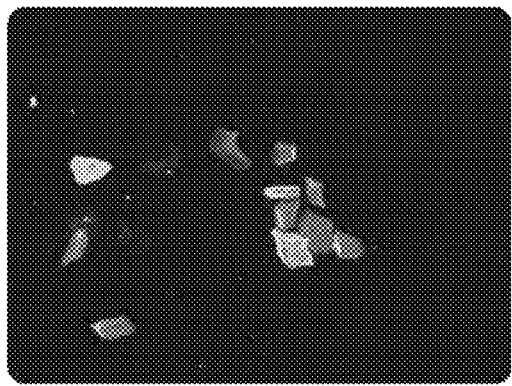
Figure 2A:
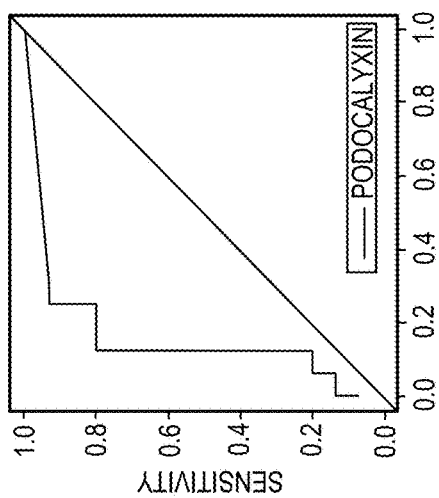
FIGS. 2A-2D contain graph plotting ROC curves for podocyturea as determined by staining for podocin (FIG. 2A), podocalyxin (FIG. 2B), nephrin (FIG. 2C), and synaptopodin (FIG. 2D) immunoreactivity.
Figure 2B:
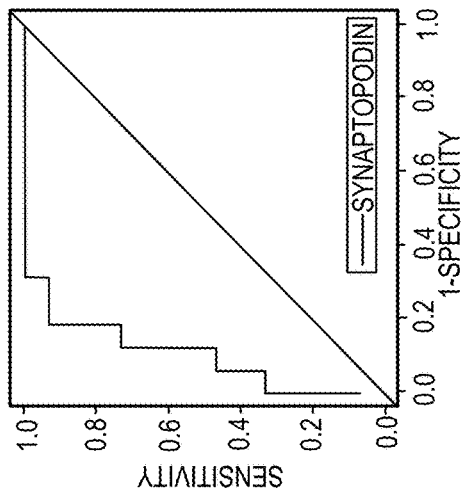
Figure 2C:
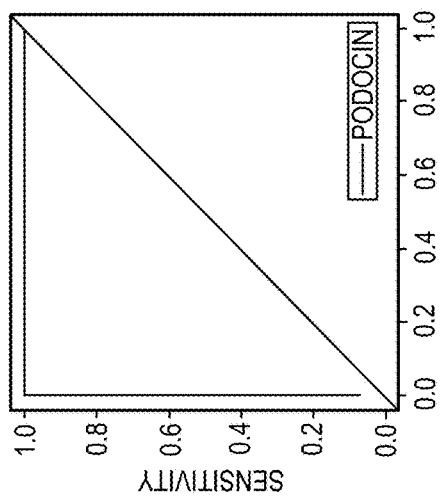
Figure 2D:
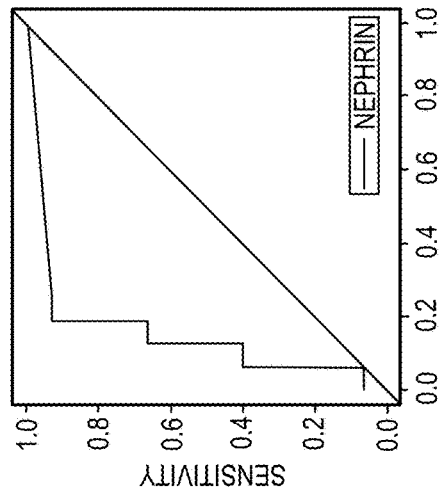
Figure 4A:
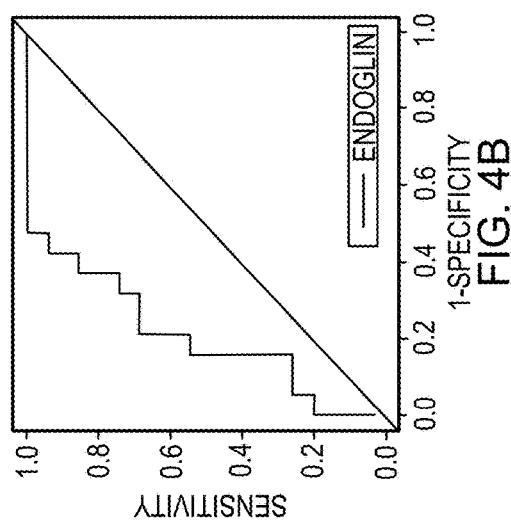
FIGS. 4A-4D contain graphs plotting ROC curves for sFlt-1 (FIG. 4A), soluble endoglin (FIG. 4B), serum PIGF (FIG. 4C), and urine PIGF (FIG. 4D).
Figure 4B:
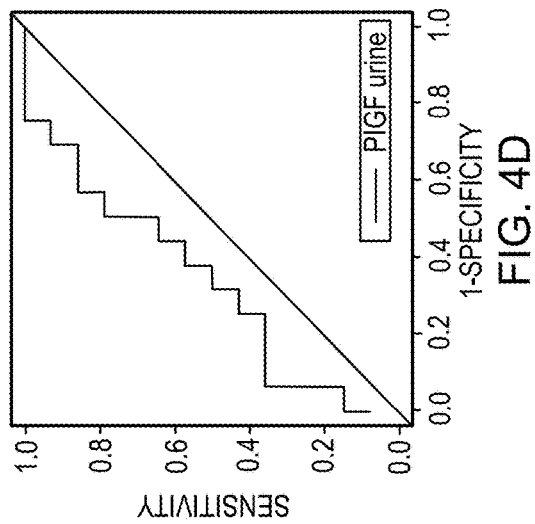
Figure 4C:
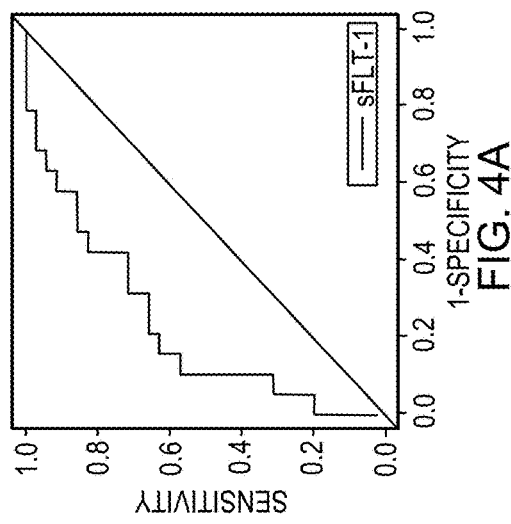
Figure 4D:
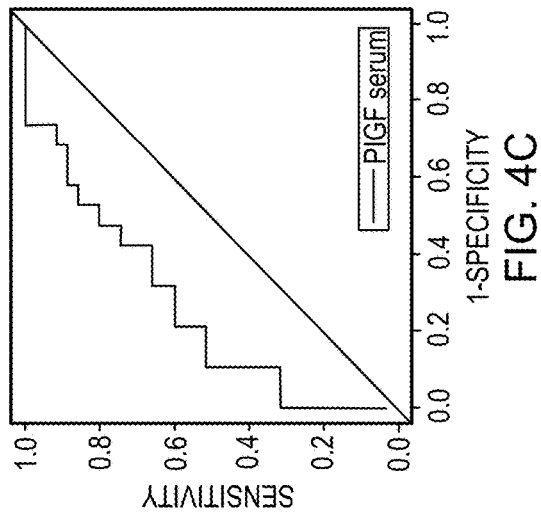

Compared with podocin, measurements of podocyturia that were based on podocalyxin, nephrin, and synaptopodin stains (FIGS. 1B, C, and D, respectively) had both lower sensitivity and specificity (Table 2). For sFLT-1, endoglin, and PlGF, the sensitivity and specificity were calculated twice, with two different cutoffs to define a positive test. The cutoffs for podocyturia (podocin, nephrin, podocalyxin, and synaptopodin) were expressed as cells per milligram of creatinine (Table 2). The ROC curves for all four podocyte markers were generated (FIG. 2), and their respective areas under the curve were compared as a measure of diagnostic accuracy.

TABLE 2

Test characteristics for markers of preeclampsia.

| | | | | Pretest probability for preeclampsia | | | |
|---|---|---|---|---|---|---|---|
| | | | | 5% | | 25% | |
| Test | Cutoff | Sensitivity (%) | Specificity (%) | Positive predictive value (%) | Negative predictive value (%) | Positive predictive value (%) | Negative predictive value (%) |
| sFLT-1* | 7463 pg/mL | 83 | 58 | 9.4 | 98.5 | 39.7 | 91.1 |
|  | 9795 pg/mL | 71 | 68 | 10.5 | 97.8 | 42.5 | 87.6 |
| Endoglin* | 21.3 ng/mL | 94 | 58 | 10.5 | 99.5 | 42.7 | 96.7 |
|  | 24.6 ng/mL | 86 | 63 | 10.9 | 98.8 | 43.7 | 93.1 |
| Serum PlGF† | 84.92 pg/mL | 74 | 58 | 8.5 | 97.7 | 37.0 | 87.0 |
|  | 102.7 pg/mL | 86 | 47 | 7.9 | 98.5 | 35.1 | 91.0 |
| Urine PlGF† | 1.22 pg/mL‡ | 79 | 50 | 7.7 | 97.8 | 34.5 | 87.7 |
|  | 2.18 pg/mL† | 86 | 38 | 7.5 | 98.4 | 33.9 | 90.4 |
| Podocin* | 0.85 cells† | 100 | 100 | 100.0 | 100.0 | 100.0 | 100.0 |
| Nephrin* | 0.75 cells† | 93 | 75 | 16.4 | 99.5 | 55.4 | 97.0 |
| Podocalyxin* | 0.83 cells† | 93 | 75 | 16.4 | 99.5 | 55.4 | 97.0 |
| Synaptopodin* | 1.11 cells† | 93 | 81 | 20.5 | 99.5 | 62.0 | 97.2 |

*A positive test is defined as having a value higher than the cutoff.
†A positive test has a lower value than the cutoff.
‡Expressed per milligram of creatinine in the respective urine samples The analysis indicated that podocin had a greater diagnostic accuracy than did podocalyxin (P=0.04) or nephrin (P=0.05) and possibly better than did synaptopodin (P=0.08); diagnostic accuracy of the other three markers (podocalyxin, nephrin, and synaptopodin) did not differ. For the cases, the rate of podocyte excretion, which was expressed as median cell number per milligram of creatinine, was 3.7 for podocin and synaptopodin, 5.0 for podocalyxin, and 3.3 for nephrin. For the control subjects, the rate of podocyte excretion for synaptopodin was 0.6, and 0 for podocalyxin, podocin, and nephrin. An additional control group consisted of women with gestational hypertension (n=6), essential hypertension (n=2), and preexisting proteinuria (n=3), who did not have clinical signs and symptoms of superimposed preeclampsia. None of these 11 women demonstrated podocyturia, as determined by podocin staining.

Angiogenic Markers of Preeclampsia

Serum sFlt-1 levels were significantly higher in women with preeclampsia or HELLP than in normotensive pregnant control subjects (17,326±12,124 pg/mL vs. 8,160±5,186 pg/mL; P<0.001; Table 3). SerumsFlt-1 levels did not differ significantly between patients with preeclampsia and HELLP (P=0.11). Patients with preeclampsia and HELLP displayed higher sFlt-1 levels than normal patients, if they delivered early in pregnancy (FIG. 3A). This difference became less apparent closer to full term delivery.

Serum soluble endoglin levels were significantly higher in women with preeclampsia or HELLP than in normotensive pregnant control subjects (55.4±31.6 ng/mL vs. 27.2±23.9 ng/mL; P<0.001). Serum soluble endoglin levels did not differ significantly between patients with preeclampsia and HELLP (P=0.69). The difference between normal and preeclamptic pregnancies was greater with an earlier delivery and became less apparent in those patients who were delivered at full term (FIG. 3B).

Serum-free PlGF levels were lower in women with preeclampsia or HELLP than in normotensive pregnant control subjects (64.6±44.7 pg/mL vs. 173±174.8 pg/mL; P=0.0005). Serum-free PlGF levels did not differ significantly between patients with preeclampsia and HELLP (P=0.36). In those patients delivering at an earlier gestational age, free PlGF levels were lower in patients with preeclampsia and HELLP vs. control subjects, but this difference became less apparent as pregnancies were carried towards full term (FIG. 3C).

There was a statistically insignificant trend towards lower urine PlGF levels in women with preeclampsia or HELLP, compared with normotensive pregnant control subjects (1.17±1.54 pg/mL/mg vs. 2.94±3.56 pg/mL/mg creatinine; P=0.11; Table 3). Urine PlGF levels in women with preeclampsia were not different than in normal women, regardless of gestational age at delivery (FIG. 3D).

TABLE 3

Normal and preeclamptic levels of sFLT-1, endoglin, and PlGF.

| Variable | Normal (n = 23) | Preeclampsia (n = 33) | HELLP (n = 11) | Preeclampsia + HELLP (n = 44) |
|---|---|---|---|---|
| sFLT-1 (pg/mL) | 8160 ± 5186 | 18,231 ± 11,216* | 14,711 ± 14,876* | 17,326 ± 12,124* |
| Endoglin (ng/mL) | 27.2 ± 23.9 | 56.5 ± 31.7* | 52.1 ± 32.7* | 55.4 ± 31.6* |
| Serum PlGF (pg/mL) | 173 ± 175 | 66.2 ± 44.2* | 59.8 ± 48.5* | 64.6 ± 44.7* |
| Urine PlGF (pg/mL per mg creatinine) | 2.94 ± 3.56 | 1.17 ± 1.54 | † | † |

Data are given as mean ± SD.
* P < 0.05, compared with normal group.
† None of the 11 patients with HELLP had urine samples.

Angiogenic Factors as Diagnostic Tests for Preeclampsia: Comparison to Podocyturia ROC curves were generated for sFlt-1, soluble endoglin, and both serum and urine PlGF (FIG. 4). The positive predictive value and the negative predictive value for podocyturia, as determined by the four podocyte-specific markers and the angiogenic factors that were evaluated (Table 2), were calculated. Because the value of a diagnostic test can depend on the pretest probability of disease, the diagnostic accuracy of each test was estimated for two different pretest probabilities: 5%, which reflects the pretest probability for preeclampsia in the general population, and 25%, which is a commonly cited percentage risk in women with preexisting hypertension. The negative predictive value did not differ between the podocyturia and angiogenic factor tests in patients with a low (5%) pretest probability. However, in patients with a pretest probability of 25%, the negative predictive value was higher with podocyturia. The positive predictive value was higher with podocyturia, compared with angiogenic factors tests in both the low and high pretest probability groups.

The results provided herein demonstrate that podocyturia (i.e., urinary excretion of podocytes) is present in patients with preeclampsia at the time of delivery. These cells retain the ability to attach to tissue culture plates in vitro, which indicates that they are viable. Urinary shedding of podocytes may contribute to proteinuria in preeclampsia, because these cells have a very limited regenerative capacity. Therefore, podocyturia may indicate podocyte loss from the glomerulus which may lead to a disruption of the glomerular filtration barrier and consequent proteinuria.

Podocyturia is present at the time of the clinical diagnosis of preeclampsia, and the number of podocytes can correlate with the degree of proteinuria. Urinary podocyte excretion, which was quantified by four podocyte-specific markers (namely, podocalyxin, podocin, nephrin, and synaptopodin), is a sensitive marker of renal damage and proteinuria in preeclampsia. Among these four markers, podocin exhibited a high sensitivity and specificity of 100% each. In addition, a positive correlation between the degree of proteinuria and podocyturia was found, which suggests a possible common/shared underlying pathogenic mechanism. Women with normotensive pregnancies and women with either hypertension or proteinuria, but in the absence of the clinical syndrome of preeclampsia, did not have podocyturia. Therefore, podocyturia does not appear to be merely a result of hypertensive kidney damage or a marker of proteinuria.

There are several possible explanations for podocin being a better marker for podocyturia in preeclampsia than podocalyxin, nephrin, or synaptopodin. Staining for podocalyxin, nephrin, and synaptopodin may be less specific, because these proteins, unlike podocin, are expressed in cells other than podocytes. These cells might be present in the urine particularly around the time of delivery, when urine samples can be contaminated with decidual, amniotic, and red and white blood cells. Moreover, staining for podocin may be more sensitive than staining for other podocyte proteins. Glomerular expression of nephrin and synaptopodin, but not podocin, was found to be decreased in kidney sections from women with preeclampsia. Consequently, podocytes that are shed in the urine may have lower expressions of nephrin and synaptopodin than podocin, which makes the latter a more sensitive marker of podocyte presence in the urine. It is particularly intriguing to postulate that podocyturia, as a marker of subclinical renal damage, may be detected before overt proteinuria and the full clinical picture of preeclampsia develops.

The results provided herein demonstrate that differences in sFlt-1, PlGF, and soluble endoglin levels between normotensive and preeclamptic pregnancies were greatest in those women who delivered earliest. Early delivery was a marker of severe disease that resulted in termination of pregnancy. These differences become less apparent as pregnancies are carried toward full term. There is a significant overlap in free PlGF and sFlt-1 values between mild forms of preeclampsia and normotensive pregnancies closer to full term, which could lead potentially to both false-positive and false-negative screening test results. In addition, no difference in urinary PlGF was observed between the cases (n=15) and control subjects (n=16), and no significant difference in circulating endoglin levels was observed between the cases of preeclampsia (n=33) and HELLP (n=11).

In summary, the results provided herein indicated that podocyturia is a marker of renal damage and proteinuria in preeclampsia.

Example 2—Detecting Levels of Microvesicles Expressing VEGFR-1

Blood and urine samples were collected from 8 preeclamptic women and 15 normal pregnant women just prior to delivery (IRB #166-00). The patient characteristics are provided in Table 4.

TABLE 4

Baseline patient characteristics

| Variable | Normal pregnancy (n = 15) | Preeclampsia (n = 8) |
| --- | --- | --- |
| Age (yrs)—mean (range) | 29.0 (19-40) | 27.3 (21-38) |
| Gestational age* (wks)—mean (range) | 38.9 (36-41) | 31.1 (27-34) |
| MAP (mm Hg)—mean (range) | 80.5 (74-88) | 108.3 (75-127) |

*At time of enrollment

Isolation of Blood Microvesicles

Blood was drawn through a 19 gauge needle into tubes containing anticoagulants, hirudin and soybean trypsin inhibitor (which inactivates platelets). Plasma was separated by centrifugation (3000×g for 15 minutes, twice) to obtain platelet free plasma. The absence of platelets in the plasma was validated by Coulter counter (platelet count≤1), and flow cytometry (FACS Canto™) using fluorescent beads (1 μm and 2 μm).

The cell free, platelet-free plasma sample (0.5 μL) was centrifuged (20,000× g for 30 minutes), and the supernatant was removed. The pellet obtained was reconstituted with 0.5 mL of 20 mM HEPES/HANK'S/0.05% glucose buffer (pH 7.4) which had been filtered using 0.2 μm pore size membrane filter. The sample was washed by vortexing, and centrifuged (20,000× g for 30 minutes). After the final centrifugation, buffer was discarded, and the pellet was reconstituted with 0.5 mL fresh buffer. The sample was vortexed for 1-2 minutes to detach microvesicles from the sides of the tube and to separate microvesicles from each other.

Staining of Blood Microvesicles

The microvesicle preparation was placed into flow cytometry tubes in 50 μL aliquots. Antibodies were added, based on the cell or receptor of interest, and incubated for 30 minutes. Antibody concentration needed for optimal staining was determined by experimentation. Anti-CD42a-PE mouse anti-human monoclonal antibodies (GPIX, BD) were used to label platelet-derived microvesicles. Anti-CD62e PE mouse anti-human monoclonal antibodies (e-selectin, BD) were used to identify endothelium-derived microvesicles. Anti-VEGFR-1 PE mouse anti-human monoclonal antibodies (R&D) were used to label VEGFR-1. Annexin V mouse anti-human monoclonal antibodies (BD) and anti-B48/B100 mouse anti-human monoclonal antibodies (AbCam) were used as markers of phospatidylserine and lipid expression. Controls were run for each sample using same isotype IgG FITC or PE stained samples.

Identification of Blood Microvesicles

Flow cytometry (FACSCanto™) was used to detect microvesicles by size and positive antibody fluorescence. Gates to define size were set using an internal standard of 1 µm and 2 µm beads (FIG. 5). For quantification, samples were spiked with a known quantity of beads of 4.2 µm diameter (FIG. 5). All buffers and antibodies were filtered through a 0.2 µm pore size membrane filter to eliminate chemical particles and to reduce instrument noise.

Separation and Quantification of Microvesicles Based on Staining

The absolute numbers of annexin-V microvesicles were calculated based on counts of calibration beads. The absolute count of microvesicles equaled the number of events in the microvesicle gate per number of events in the calibration bead region as multiplied by the number of beads per test (spiked known count/test volume). The same calculation was applied to quantification of microvesicles positive or negative for annexin-V or other cell specific monoclonal antibodies.

Data Analysis

Data were analyzed using Microsoft Excel. The diagnosis of preeclampsia was made in the presence of hypertension accompanied by proteinuria, as recommended elsewhere (*Am J Obstet Gynecol* 183(1): S1-S22 (2000)). Hypertension was defined as blood pressure of 140/90 mmHg; excretion of 300 mg of protein or more in a 24-hour urine specimen was considered diagnostic of significant proteinuria.

Results

Preeclamptic women had median (inter-quartile range) proteinuria (mg/24 hour) of 1466 (561-2642). A portion of plasma microvesicles expressed VEGFR-1 in both preeclamptic and normal pregnant women. VEGFR-1 positive microvesicles were significantly elevated in preeclamptic as compared to normal pregnant women. VEGFR-1 positive microvesicles were 30.0 (14.3-81.0) microvesicles per liter plasma in preeclamptic women as compared to 12.0 (8.0-14.0) microvesicles per liter plasma in normal pregnant women (p=0.01 by Wilcoxon rank sum test). There was not a statistically significant difference in total microvesicles per liter plasma between the two groups: 327 (289-509) in preeclamptic women vs. 333 (232-385) in normal pregnant women (p=0.54 by Wilcoxon rank sum test).

In summary, the results provided herein indicated that an increased level of VEGFR-1 expressing microvesicles is associated with preeclampsia in women.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for avoiding unnecessary treatment of preeclampsia, said method comprising:
    (a) contacting a urine sample collected from a pregnant human during gestational week 18 to 36 with an antibody under conditions that allow binding of said antibody to a podocyte or a fragment of said podocyte, wherein, when said urine sample contains podocytes or fragments of said podocytes, antibody complexes comprising said antibody and said podocyte or a fragment of said podocyte are formed,
    (b) detecting an absence of an elevated level of said antibody complexes as compared to corresponding urine levels from pregnant humans lacking preeclampsia, and
    (c) proceeding with treatment of said pregnant human in a manner that avoids unnecessary treatment of preeclampsia based on the urine levels of said antibody complexes detected in step (a) in said pregnant human.

2. The method of claim 1, wherein said antibody is an anti-podocin antibody.

3. The method of claim 1, wherein said antibody is an anti-podocalyxin antibody.

4. The method of claim 1, wherein said antibody is an anti-nephrin antibody.

5. The method of claim 1, wherein said antibody is an anti-synaptopodin antibody.

* * * * *